US009610319B2

(12) United States Patent
Holford et al.

(10) Patent No.: US 9,610,319 B2
(45) Date of Patent: Apr. 4, 2017

(54) METHOD OF TREATING CANCER

(71) Applicant: Research Foundation of the City University of New York, New York, NY (US)

(72) Inventors: Mande Holford, New York, NY (US); Prachi Anand, New York, NY (US); Beatrix Ueberheide, New York, NY (US); Brian Chait, New York, NY (US)

(73) Assignees: Research Foundation of the City University of New York, New York, NY (US); The Rockefeller University, New York, NY (US)

( * ) Notice: Subject to any disclaimer, the term of this patent is extended or adjusted under 35 U.S.C. 154(b) by 0 days.

(21) Appl. No.: 14/870,271

(22) Filed: Sep. 30, 2015

(65) Prior Publication Data

US 2016/0089416 A1    Mar. 31, 2016

Related U.S. Application Data

(60) Provisional application No. 62/057,335, filed on Sep. 30, 2014.

(51) Int. Cl.
*A61K 38/10* (2006.01)
*A61K 38/00* (2006.01)
*C07K 7/00* (2006.01)
*C07K 7/08* (2006.01)
*C07K 14/00* (2006.01)
*A61K 38/17* (2006.01)

(52) U.S. Cl.
CPC .......... *A61K 38/10* (2013.01); *A61K 38/1767* (2013.01)

(58) Field of Classification Search
CPC .......... A61K 38/10; A61K 38/00; C07K 7/00; C07K 4/08; C07K 14/001; C07K 7/08; C07K 14/00
USPC ........................................................ 514/19.3
See application file for complete search history.

(56) References Cited

U.S. PATENT DOCUMENTS

2008/0131421 A1* 6/2008 Scarlato ................. C07K 14/22
424/130.1

OTHER PUBLICATIONS

A0A0B4J184 from UniProt, pp. 1-5. Accessed Jun. 21, 2016.*
Rudinger J, "Characteristics of the amino acids as components of a peptide hormone sequence," Peptide Hormones, JA Parsons Edition, University Park Press, Jun. 1976, pp. 1-7.*
"Designing Custom Peptides," from SIGMA Genosys, pp. 1-2. Accessed Dec. 16, 2004.*
Schinzel R, Drueckes P, "The phosphate recognition site of *Escherichia coli* maltodextrin phosphorylase," FEBS, Jul. 1991, 286(1,2): 125-128.*
Berendsen HJC, "A Glimpse of the Holy Grail?" Science, 1998, 282: 642-643.*
Voet D, Voet JG, Biochemistry, Second Edition, John Wiley & Sons, Inc., 1995, pp. 235-241.*
Ngo JT, Marks J, Karplus M, "Computational Complexity, Protein Structure Prediction, and the Levinthal Paradox," The Protein Folding Problem and Tertiary Structure Prediction, K. Merc Jr. and S. Le Grand Edition, 1994, pp. 491-495.*
Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.*
Yampolsky et al., "The Exchangeability of Amino Acids in Proteins," Genetics, Aug. 2005, 170: 1459-1472.*
Anand, Prachi et al.; Sample Limited Characterization of a Novel Disulfide-Rich Venom Peptide Toxin from Terebrid Marine Snail; PLOS One, Apr. 8, 2014; vol. 9, Issue 4; e94122; pp. 1-9; US.
Vetter, Irina et al.; Therapeutic Potential of Cone Snail Venom Peptides (Conopeptides); Current Topics in Medicinial Chemistry; 2012, pp. 1546-1552; vol. 12, US.
Miljanich, G.P. Ziconotide: Neuronal Calcium Channel Blocker for Treating Severe Chronic Pain; Current Medicinal Chemistry, Dec. 2004; pp. 3029-3040; vol. 11, Issue 23, US.
Dutertre, Sebastien et al.; Use of Venom Peptides to Probe Ion Channel Structure and Function; The Journal of Biological Chemistry vol. 285, No. 18, pp. 13315-13320, Apr. 30, 2010; The American Society for Biochemistry and Molecular Biology, Inc., US.
Jacob, Reed et al.; The M-superfamily of conotoxins: a review; Cell Mol Life Sci.; Jan. 2010; vol. 67, Issue 1 pp. 17-27; US.
Kendel, Yvonne et al.; Venomous Secretions from Marine Snails of the Terebridae Family Target Acetylcholine Receptors; Toxins; May 21, 2013; pp. 1043-1050; vol. 5, Issue 5; US.
Holford, Mande et al.; Pruning Nature: Biodiversity-Derived Discovery of Novel Sodium Channel Blocking Conotoxins from Conus bullatus; Toxicon; Jan. 2009; pp. 90-98; vol. 53, Issue 1; US.
Castelin, M. et al.; Macroevolution of venom apparatus innovations in auger snails (*Gastropoda; Conoidea; Terebridae*); Mol Phylogenet Evol.; Jul. 2012; pp. 21-44; vol. 64, Issue 1; US.
Holford, Mande et al.; Evolution of the Toxoglossa Venom Apparatus as Inferred by Molecular Phylogeny of the Terebridae; Mol. Biol. Evol. ; Oct. 6, 2008; pp. 15-25; vol. 26, Issue 1; US.
Puillandre, Nicolas et al.; The Terebridae and teretoxins: Combining phylogeny and anatomy for concerted discovery of bioactive compounds; BMC Chemical Biology; Sep. 17, 2010; pp. 1-12 vol. 10, Issue 7; US.
Prashanth, Jutty Rajan et al.; Towards an integrated venomics approach for accelerated conopeptide discovery; Toxicon; Apr. 28, 2012; pp. 470-477; vol. 60, Issue 6,; US.

(Continued)

*Primary Examiner* — Julie Ha
(74) *Attorney, Agent, or Firm* — Peter J. Miksell; Schmeiser, Olsen & Watts, LLP (57) ABSTRACT

A method of treating liver cancer using a peptide based on venom from a terebrid snail, terebrid variegata, is described. The venom has a general formula of TRX$_3$CCGCYWNGSKDVCSQSCC (SEQ ID NO: 1) and variants thereof are described.

7 Claims, 1 Drawing Sheet

(56) References Cited

OTHER PUBLICATIONS

Favreau, Philippe et al.; Marine snail venoms: use and trends in receptor and channel neuropharmacology; ScienceDirect; Jun. 18, 2009; pp. 594-601; vol. 9; US.

Corpuz, Gloria P. et al.; Definition of the M-Conotoxin Superfamily: Characterization of Novel Peptides from Molluscivorous Conus Venoms; Biochemistry; Jun. 7, 2005; pp. 8176-8186; vol. 44; American Chemical Society; US.

King, Glenn F.; Venoms as a platform for human drugs; translating toxins into therapeutics; Expert Opin Biol Ther.; Sep. 23, 2011; pp. 1469-1484; vol. 11; Informa UK Ltd. UK.

* cited by examiner

KIIIA

FIG. 1B

SmIIIA

SEQUENCE LISTING

```
<160> NUMBER OF SEQ ID NOS: 6

<210> SEQ ID NO 1
<211> LENGTH: 21
<212> TYPE: PRT
<213> ORGANISM: Terebra variegata
<220> FEATURE:
<221> NAME/KEY: Var
<222> LOCATION: (3)..(3)
<223> OTHER INFORMATION: I or L

<400> SEQUENCE: 1

Thr Arg Xaa Cys Cys Gly Cys Tyr Trp Asn Gly Ser Lys Asp Val Cys
1               5                   10                  15

Ser Gln Ser Cys Cys
            20

<210> SEQ ID NO 2
<211> LENGTH: 21
<212> TYPE: PRT
<213> ORGANISM: Terebra variegata

<400> SEQUENCE: 2

Thr Arg Ile Cys Cys Gly Cys Tyr Trp Asn Gly Ser Lys Asp Val Cys
1               5                   10                  15

Ser Gln Ser Cys Cys
            20

<210> SEQ ID NO 3
<211> LENGTH: 21
<212> TYPE: PRT
<213> ORGANISM: Terebra variegata

<400> SEQUENCE: 3

Thr Arg Leu Cys Cys Gly Cys Tyr Trp Asn Gly Ser Lys Asp Val Cys
1               5                   10                  15

Ser Gln Ser Cys Cys
            20

<210> SEQ ID NO 4
<211> LENGTH: 21
<212> TYPE: PRT
<213> ORGANISM: Artificial Sequence
<220> FEATURE:
<223> OTHER INFORMATION: Completely synthetic peptide based on SEQ ID
      NO: 1 from terebrid variegata
<220> FEATURE:
<221> NAME/KEY: VARIANT
```

```
<222> LOCATION: (1)..(1)
<223> OTHER INFORMATION: S, T, N or Q
<220> FEATURE:
<221> NAME/KEY: VARIANT
<222> LOCATION: (1)..(1)
<223> OTHER INFORMATION: S, T, N or Q
<220> FEATURE:
<221> NAME/KEY: VARIANT
<222> LOCATION: (1)..(1)
<223> OTHER INFORMATION: S, T, N or Q
<220> FEATURE:
<221> NAME/KEY: VARIANT
<222> LOCATION: (2)..(2)
<223> OTHER INFORMATION: R, H or K
<220> FEATURE:
<221> NAME/KEY: VARIANT
<222> LOCATION: (3)..(3)
<223> OTHER INFORMATION: A, I, L, M, F, W, Y, O, P or V
<220> FEATURE:
<221> NAME/KEY: VARIANT
<222> LOCATION: (4)..(4)
<223> OTHER INFORMATION: C or U
<220> FEATURE:
<221> NAME/KEY: VARIANT
<222> LOCATION: (5)..(5)
<223> OTHER INFORMATION: C or U
<220> FEATURE:
<221> NAME/KEY: VARIANT
<222> LOCATION: (7)..(7)
<223> OTHER INFORMATION: C or U
<220> FEATURE:
<221> NAME/KEY: VARIANT
<222> LOCATION: (8)..(8)
<223> OTHER INFORMATION: A, I, L, M, F, W, Y, O, P or V
<220> FEATURE:
<221> NAME/KEY: VARIANT
<222> LOCATION: (9)..(9)
<223> OTHER INFORMATION: A, I, L, M, F, W, Y, O, P or V
<220> FEATURE:
<221> NAME/KEY: VARIANT
<222> LOCATION: (10)..(10)
<223> OTHER INFORMATION: S, T, N or Q
<220> FEATURE:
<221> NAME/KEY: VARIANT
<222> LOCATION: (12)..(12)
<223> OTHER INFORMATION: S, T, N or Q
<220> FEATURE:
<221> NAME/KEY: VARIANT
<222> LOCATION: (13)..(13)
<223> OTHER INFORMATION: R, H or K
<220> FEATURE:
<221> NAME/KEY: VARIANT
<222> LOCATION: (14)..(14)
<223> OTHER INFORMATION: D or E
<220> FEATURE:
<221> NAME/KEY: VARIANT
<222> LOCATION: (15)..(15)
<223> OTHER INFORMATION: A, I, L, M, F, W, Y, O, P or V
<220> FEATURE:
<221> NAME/KEY: VARIANT
<222> LOCATION: (16)..(16)
<223> OTHER INFORMATION: C or U
<220> FEATURE:
<221> NAME/KEY: VARIANT
<222> LOCATION: (17)..(17)
<223> OTHER INFORMATION: S, T, N or Q
<220> FEATURE:
<221> NAME/KEY: VARIANT
<222> LOCATION: (18)..(18)
<223> OTHER INFORMATION: S, T, N or Q
<220> FEATURE:
<221> NAME/KEY: VARIANT
<222> LOCATION: (19)..(19)
<223> OTHER INFORMATION: S, T, N or Q
<220> FEATURE:
<221> NAME/KEY: VARIANT
<222> LOCATION: (20)..(20)
<223> OTHER INFORMATION: C or U
<220> FEATURE:
```

```
<221> NAME/KEY: VARIANT
<222> LOCATION: (21)..(21)
<223> OTHER INFORMATION: C or U

<400> SEQUENCE: 4

Xaa Xaa Xaa Xaa Xaa Gly Xaa Xaa Xaa Xaa Gly Xaa Xaa Xaa Xaa Xaa
1               5                   10                  15

Xaa Xaa Xaa Xaa Xaa
            20

<210> SEQ ID NO 5
<211> LENGTH: 18
<212> TYPE: PRT
<213> ORGANISM: Artificial Sequence
<220> FEATURE:
<223> OTHER INFORMATION: Completely synthetic peptide based on SEQ ID
      NO: 1 from terebrid variegata
<220> FEATURE:
<221> NAME/KEY: VARIANT
<222> LOCATION: (1)..(1)
<223> OTHER INFORMATION: C or U
<220> FEATURE:
<221> NAME/KEY: VARIANT
<222> LOCATION: (2)..(2)
<223> OTHER INFORMATION: C or U
<220> FEATURE:
<221> NAME/KEY: VARIANT
<222> LOCATION: (4)..(4)
<223> OTHER INFORMATION: C or U
<220> FEATURE:
<221> NAME/KEY: VARIANT
<222> LOCATION: (5)..(5)
<223> OTHER INFORMATION: A, I, L, M, F, W, Y, O, P or V
<220> FEATURE:
<221> NAME/KEY: VARIANT
<222> LOCATION: (6)..(6)
<223> OTHER INFORMATION: A, I, L, M, F, W, Y, O, P or V
<220> FEATURE:
<221> NAME/KEY: VARIANT
<222> LOCATION: (7)..(7)
<223> OTHER INFORMATION: S, T, N or Q
<220> FEATURE:
<221> NAME/KEY: VARIANT
<222> LOCATION: (9)..(9)
<223> OTHER INFORMATION: S, T, N or Q
<220> FEATURE:
<221> NAME/KEY: VARIANT
<222> LOCATION: (10)..(10)
<223> OTHER INFORMATION: R, H or K
<220> FEATURE:
<221> NAME/KEY: VARIANT
<222> LOCATION: (11)..(11)
<223> OTHER INFORMATION: D or E
<220> FEATURE:
<221> NAME/KEY: VARIANT
<222> LOCATION: (12)..(12)
<223> OTHER INFORMATION: A, I, L, M, F, W, Y or V
<220> FEATURE:
<221> NAME/KEY: VARIANT
<222> LOCATION: (13)..(13)
<223> OTHER INFORMATION: C or U
<220> FEATURE:
<221> NAME/KEY: VARIANT
<222> LOCATION: (14)..(14)
<223> OTHER INFORMATION: S, T, N or Q
<220> FEATURE:
<221> NAME/KEY: VARIANT
<222> LOCATION: (15)..(15)
<223> OTHER INFORMATION: S, T, N or Q
<220> FEATURE:
<221> NAME/KEY: VARIANT
<222> LOCATION: (16)..(16)
<223> OTHER INFORMATION: S, T, N or Q
<220> FEATURE:
<221> NAME/KEY: VARIANT
<222> LOCATION: (17)..(17)
```

```
<223> OTHER INFORMATION: C or U
<220> FEATURE:
<221> NAME/KEY: VARIANT
<222> LOCATION: (18)..(18)
<223> OTHER INFORMATION: C or U

<400> SEQUENCE: 5

Xaa Xaa Gly Xaa Xaa Xaa Xaa Gly Xaa Xaa Xaa Xaa Xaa Xaa Xaa
1               5                   10                  15

Xaa Xaa

<210> SEQ ID NO 6
<211> LENGTH: 18
<212> TYPE: PRT
<213> ORGANISM: Artificial Sequence
<220> FEATURE:
<223> OTHER INFORMATION: Completely synthetic peptide based on SEQ ID
      NO: 1 from terebrid variegata
<220> FEATURE:
<221> NAME/KEY: VARIANT
<222> LOCATION: (5)..(5)
<223> OTHER INFORMATION: A, I, L, M, F, W, Y, O, P or V
<220> FEATURE:
<221> NAME/KEY: VARIANT
<222> LOCATION: (6)..(6)
<223> OTHER INFORMATION: A, I, L, M, F, W, Y, O, P or V
<220> FEATURE:
<221> NAME/KEY: VARIANT
<222> LOCATION: (7)..(7)
<223> OTHER INFORMATION: S, T, N or Q
<220> FEATURE:
<221> NAME/KEY: VARIANT
<222> LOCATION: (9)..(9)
<223> OTHER INFORMATION: S, T, N or Q
<220> FEATURE:
<221> NAME/KEY: VARIANT
<222> LOCATION: (10)..(10)
<223> OTHER INFORMATION: R, H or K
<220> FEATURE:
<221> NAME/KEY: VARIANT
<222> LOCATION: (11)..(11)
<223> OTHER INFORMATION: D or E
<220> FEATURE:
<221> NAME/KEY: VARIANT
<222> LOCATION: (12)..(12)
<223> OTHER INFORMATION: A, I, L, M, F, W, Y or V
<220> FEATURE:
<221> NAME/KEY: VARIANT
<222> LOCATION: (14)..(14)
<223> OTHER INFORMATION: S, T, N or Q
<220> FEATURE:
<221> NAME/KEY: VARIANT
<222> LOCATION: (15)..(15)
<223> OTHER INFORMATION: S, T, N or Q
<220> FEATURE:
<221> NAME/KEY: VARIANT
<222> LOCATION: (16)..(16)
<223> OTHER INFORMATION: S, T, N or Q

<400> SEQUENCE: 6

Cys Cys Gly Cys Xaa Xaa Xaa Gly Xaa Xaa Xaa Xaa Cys Xaa Xaa Xaa
1               5                   10                  15

Cys Cys
```

METHOD OF TREATING CANCER

CROSS-REFERENCE TO RELATED APPLICATIONS

This application claims priority to and is a non-provisional of U.S. Patent Application Ser. No. 62/057,335 (filed Sep. 30, 2014) the entirety of which is incorporated herein by reference.

REFERENCE TO A SEQUENCE LISTING

This application refers to a "Sequence Listing" listed below, which is provided as an electronic document entitled "Sequence_ST25.txt" (5 kb, created on Sep. 29, 2015), which is incorporated herein by reference in its entirety.

STATEMENT OF FEDERALLY SPONSORED RESEARCH OR DEVELOPMENT

This invention was made with Government support under Contract Number NSFCHE1247550 awarded by the National Science Foundation. The government has certain rights in the invention.

BACKGROUND OF THE INVENTION

The subject matter disclosed herein relates to a method for treating liver cancer. There is a need to discover new compounds that enhance the drug pipeline for treating ailments. The peptide toxins found in venomous organisms such as snakes, spiders, scorpions, leeches, and marine snails are highly efficient and effective for manipulating physiological pathways and represent a promising source of potential therapeutic agents. Peptides, while currently not as bio-available as small molecule therapeutics, have advantages of higher target specificity and selectivity, and decreased toxicity. Despite their advantages, the use of peptides in drug development lags in the discovery and characterization stages. An important obstacle in obtaining workable quantities of venomous natural products has remained a significant challenge due to the large amount of material that has traditionally been needed to identify and structurally characterize peptidic compounds. A sensitive and robust method for discovery and characterization of peptide toxins from venom sources would facilitate their application as biochemical tools and potential drug development targets.

The discussion above is merely provided for general background information and is not intended to be used as an aid in determining the scope of the claimed subject matter.

BRIEF DESCRIPTION OF THE INVENTION

This disclosure pertains to a method of treating liver cancer using a peptide based on venom from a terebrid snail, terebrid variegata. The venom has a general formula of $TRX_3CCGCYWNGSKDVCSQSCC$ (SEQ ID NO: 1) and variants thereof are described. An advantage that may be realized in the practice of some disclosed embodiments of the method resides in that the peptide selectively targets tumor cell versus normal cells in liver cancer.

In a first embodiment, a method for treating liver cancer is provided. The method comprising administering a peptide to a patient with liver cancer, the peptide comprising SEQ ID NO: 5 $(X_1X_2GX_4X_5X_6X_7GX_9X_{10}X_{11}X_{12}X_{13}X_{14}X_{15}X_{16}X_{17}X_{18})$ wherein the peptide has one hundred or fewer residues and $X_1$, $X_2$, $X_4$, $X_{13}$, $X_{17}$, and $X_{18}$ are independently selected from C or U or a corresponding non-natural amino acid thereof; $X_5$, $X_6$, and $X_{12}$ are independently selected from A, I, L, M, F, W, Y, O, P or V or a corresponding non-natural amino acid thereof; $X_7$, $X_9$, $X_{14}$, $X_{15}$ and $X_{16}$ are independently selected from S, T, N or Q or a corresponding non-natural amino acid thereof; $X_{10}$ is R, H or K; $X_{11}$ is D or E or a corresponding non-natural amino acid thereof.

In a second embodiment, a method for treating liver cancer is provided. The method comprising administering a peptide to a patient with liver cancer, the peptide comprising SEQ ID NO: 6 $(CCGCX_5X_6X_7GX_9X_{10}X_{11}X_{12}CX_{14}X_{15}X_{16}CC)$ wherein the peptide has one hundred or fewer residues and $X_5$, $X_6$, and $X_{12}$ are independently selected from A, I, L, M, F, W, Y, O, P or V; $X_7$, $X_9$, $X_{14}$, $X_{15}$ and $X_{16}$ are independently selected from S, T, N or Q; and $X_{10}$ is R, H or K; $X_{11}$ is D or E.

In a third embodiment, a method for treating liver cancer is provided. The method comprising administering a peptide to a patient with liver cancer, the peptide comprising SEQ ID NO: 1 $(TRX_3CCGCYWNGSKDVCSQSCC)$ wherein the peptide has one hundred or fewer residues and $X_3$ is I or L.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

Disclosed in this specification is an integrated method that utilizes liquid chromatography mass spectrometric sequencing, chemical peptide synthesis, and nuclear magnetic resonance (NMR) for the rapid identification and characterization of sample limited bioactive disulfide-rich venomous snail peptide toxins. The sequence and structural characterization approach presented here significantly reduces the number of organisms needed while allowing for rapid characterization of venom components.

A novel teretoxin, Tv1 (TR(I/L)CCGCYWNGSKDVC-SQSCC (SEQ ID NO: 1)) from a terebrid snail, terebrid variegata was structurally identified and found to be biologically active. Tv1 selectively targets tumor cell versus normal cells in liver cancer when applied in vitro to cell lines IMEA7 and BNL.CL2 and in vivo to mice models expressing IMEA7 tumor cells subcutaneously. Tv1 was analyzed in cell viability, immunoblotting, and wound healing assays to characterize its function on liver cancer cells. In all cases Tv1 prevented the death of normal versus cancer cells at high instance compared to commercially available routine cancer treatments, such as sorafenib and doxorubicin. Structural characterization of *Terebra variegata* peptide toxin Tv1 was accomplished using a total venom sample of 4 ng, an amount that would previously make characterization of venom components almost impossible.

TABLE 1

| | |
|---|---|
| $TRX_3CCGCYWNGSKDVCSQSCC$ | (SEQ. ID NO. 1) |
| TRICCGCYWNGSKDVCSQSCC | (SEQ. ID NO. 2) |
| TRLCCGCYWNGSKDVCSQSCC | (SEQ. ID NO. 3) |

Variants of SEQ ID NO: 1, including but not limited to SEQ ID NO: 2 and SEQ ID NO: 3, are also possible. See SEQ ID NO: 4. In one embodiment, the peptide has at least ten residues and one-hundred or fewer residues. In another embodiment, the peptide has at least ten residues and fifty or fewer residues.

XXXXXGXXXXGXXXXXXXXXX (SEQ. ID NO. 4)

| Position | Residue | Examples | Tv1 |
|---|---|---|---|
| 1 | Polar | S, T, N or Q | T |
| 2 | Positive | R, H or K | R |
| 3 | Non-polar | A, I, L, M, F, W, Y, O, P or V | I |
| 4 | Cystine/ Selenocystein | C, U | C |
| 5 | Cystine/ Selenocystein | C, U | C |
| 6 | Glycine | G | G |
| 7 | Cystine/ Selenocystein | C, U | C |
| 8 | Non-polar | A, I, L, M, F, W, Y, O, P or V | Y |
| 9 | Non-polar | A, I, L, M, F, W, Y, O, P or V | W |
| 10 | Polar | S, T, N or Q | N |
| 11 | Glycine | G | G |
| 12 | Polar - no charge | S, T, N or Q | S |

-continued

XXXXXGXXXXGXXXXXXXXXX (SEQ. ID NO. 4)

| Position | Residue | Examples | Tv1 |
|---|---|---|---|
| 13 | Positive | R, H or K | K |
| 14 | Negative | D or E | D |
| 15 | Non-polar | A, I, L, M, F, W, Y, O, P or V | V |
| 16 | Cystine/ Selenocystein | C, U | C |
| 17 | Polar - no charge | S, T, N or Q | S |
| 18 | Polar - no charge | S, T, N or Q | Q |
| 19 | Polar - no charge | S, T, N or Q | S |
| 20 | Cystine/ Selenocystein | C, U | C |
| 21 | Cystine/ Selenocystein | C, U | C |

In another embodiment, the peptide has at least eighteen residues and one hundred or fewer residues. See SEQ ID NO: 5. In another such embodiment, the peptide has at least eighteen residues and fifty or fewer residues. In another embodiment, the peptide has thirty or fewer residues. The peptide may comprise, consist essentially of, or consist of the disclosed sequences.

XXGXXXXGXXXXXXXXXX (SEQ. ID NO. 5)

| Position | Residue | Examples | Tv1 |
|---|---|---|---|
| 1 | Cystine/ Selenocystein | C, U | C |
| 2 | Cystine/ Selenocystein | C, U | C |
| 3 | Glycine | G | G |
| 4 | Cystine/ Selenocystein | C, U | C |
| 5 | Non-polar | A, I, L, M, F, W, Y, O, P or V | Y |
| 6 | Non-polar | A, I, L, M, F, W, Y, O, P or V | W |
| 7 | Polar | S, T, N or Q | N |
| 8 | Glycine | G | G |
| 9 | Polar - no charge | S, T, N or Q | S |
| 10 | Positive | R, H or K | K |
| 11 | Negative | D or E | D |
| 12 | Non-polar | A, I, L, M, F, W, Y or V | V |
| 13 | Cystine/ Selenocystein | C, U | C |

-continued

XXGXXXXGXXXXXXXXXX (SEQ. ID NO. 5)

| Position | Residue | Examples | Tv1 |
|---|---|---|---|
| 14 | Polar - no charge | S, T, N or Q | S |
| 15 | Polar - no charge | S, T, N or Q | Q |
| 16 | Polar - no charge | S, T, N or Q | S |
| 17 | Cystine/ Selenocystein | C, U | C |
| 18 | Cystine/ Selenocystein | C, U | C |

In the aforementioned tables, any of the naturally occurring residues may be substituted with its corresponding non-natural derivatives (e.g. hydroProline) or postmodified derivatives. Examples of non-natural amino acids include β-amino acids homolog amino acids; proline and pyruvic acid derivatives, 3-substituted alanine derivatives, glycine derivatives, ring-substituted phenylalanine and tyrosine derivatives, linear core amino acids and N-methyl amino acids.

CCGCXXXGXXXXCXXXCC (SEQ. ID NO. 6)

| Position | Residue | Examples | Tv1 |
|---|---|---|---|
| 1 | Cystine | C | C |
| 2 | Cystine | C | C |
| 3 | Glycine | G | G |
| 4 | Cystine | C | C |
| 5 | Non-polar | A, I, L, M, F, W, Y, O, P or V | Y |
| 6 | Non-polar | A, I, L, M, F, W, Y, O, P or V | W |
| 7 | Polar | S, T, N or Q | N |
| 8 | Glycine | G | G |
| 9 | Polar - no charge | S, T, N or Q | S |
| 10 | Positive | R, H or K | K |
| 11 | Negative | D or E | D |
| 12 | Non-polar | A, I, L, M, F, W, Y or V | V |
| 13 | Cystine | C | C |
| 14 | Polar - no charge | S, T, N or Q | S |
| 15 | Polar - no charge | S, T, N or Q | Q |
| 16 | Polar - no charge | S, T, N or Q | S |
| 17 | Cystine | C | C |
| 18 | Cystine | C | C |

Mouse Data

Balb/c female mice (20-35 g) were used for mouse studies. Animals were maintained on standard animal diet, in a controlled room (22±1° C. @ 35-50% RH) for a week prior to experiments. Animals were randomly divided into three groups: negative control (only PBS), high-dose and low-dose ZCD groups. Each group had five mice under sterile condition. On the day nine, the BNL.1MEA.7.R.1 cells (5 million) were injected into the right leg of each animal and allowed the tumors to grow. After two weeks the animals were checked for tumor growth and the sizes of tumors were recorded using calipers. The treatment was started after finding tumors in all groups.

The concentration of the Tv1 formulations was prepared at 0.08 mg/kg body weight (low dose) and 0.80 mg/kg body weight (high dose) for the intraperitoneal injections. Control group of animals received PBS. The drug administrations were continued for seven days and then further after a five day interval treatment was continued for another eight days and tumor sizes were measured every day.

The tumor volumes were found progressively increased in the negative control group from an average size of 156.6±20.67 $mm^3$ at day one to 809±125.87 $mm^3$ at the end of treatment which was an increase of 418%. While the average tumor volume for low dose treatment group was only increased by (180±36.74 to 485±175.07 $mm^3$) 170%. In the high-dose group, the tumor volumes were 286.08±39.9 $mm^3$ at the beginning of the treatment and were 434.28±286 $mm^3$ after the last day which is an increase of only 52%. The results showed that Tv1 is effective in significantly decreasing the growth of tumor with both low and high doses. The body weights were also monitored throughout the treatment period and they were not significantly changed.

Venom Extraction and De-Novo Sequencing of Tv1

The primary sequence characterization of Tv1 was accomplished using charge-enhanced Electron Transfer Dissociation (ETD) in combination with traditional Collisional Activated Dissociation (CAD) on reduced and alkylated *Terebra variegata* venom. The peptide toxins in the crude venom were reduced and subsequently alkylated using either iodoacetamide or N, N-dimethyl-2-chloro-ethylamine. The latter converts every cysteine residue into a dimethyl lysine analogue, which increases the charge state of each cysteine-rich peptide toxin, resulting in excellent sequence coverage with ETD.

Combining complementary dissociation strategies CAD and ETD facilitates de novo sequencing, as each dissociation strategy has specific fragmentation characteristics, which can be used to confirm the corresponding ETD and CAD spectra. This is advantageous as peptide toxin sequences can be obtained directly from crude venom without prior fractionation and using only mass spectrometry. This feature is particularly important for sequencing peptide toxins from animals producing minimal amounts of venom, such as terebrids, where only nanogram quantities are extracted from each snail specimen. Four nanograms of crude *Terebra variegata* salivary gland contents were extracted with 30% acetonitrile/water in 0.1% trifluoroacetic acid. An aliquot of the crude venom was analyzed using LC-MS on an Orbitrap XL mass spectrometer to determine the number of teretoxins present. LC-MS analysis was repeated after reduction of the crude venom to determine the number of cysteine residues present in each component. At this point, Tv1 was selected for further analysis due to its similarity in molecular weight and number of cysteines to M superfamily conotoxins. A reduced version of Tv1 was dissociated using CAD and the dimethyl lysine analogue version of the teretoxin was dissociated using ETD. The ETD MS/MS spectrum resulted in almost 100% sequence coverage. The sequence assignment by ETD could be supported with the CAD spectrum on the reduced toxin. There were two places of ambiguity in the Tv1 peptide sequence: (1) the inherent uncertainty of isoleucine (Ile) and leucine (Leu) at the third position, which cannot be differentiated with the mass spectrometer used for this analysis, and (2) the order of the first two amino acids, Thr, Arg or Arg, Thr. The second ambiguity was resolved based on the absence of the c1 ion, and the resulting Tv1 sequence was determined as TR(I/L)CCGCYWNGSKDVCSQSCC (SEQ ID NO: 1). However, the Ile/Leu ambiguity at position three could not be resolved as there was not sufficient crude extract remaining after MS characterization.

To confirm Tv1 de novo assignment, the peptide was chemically synthesized using Fmoc Solid Phase Peptide Synthesis (SPPS). Due to inherent uncertainty in the amino acid sequence at position 3, both Ile3 and Leu3 containing peptides were synthesized and subjected to the same chemical derivatization strategy. The two synthesized Tv1 teretoxins both resulted in an MS/MS spectrum identical to the native peptide, confirming the de novo sequence assignment in which TR is the order of the first two amino acids, but with remaining I/L uncertainty at position 3 due to the mass spectrometer used. The novel peptide teretoxin, Tv1 from venomous marine snail *Terebra variegata* was thus identified and its sequence was determined.

Synthesis, Characterization and Oxidative Folding of Tv1

Tv1 was chemically synthesized using Fmoc Solid Phase Peptide Synthesis without prior knowledge of disulfide connectivity, and all cysteine residues were protected with a standard side chain protecting group, trityl. The synthesized Tv1 peptide was purified to 99% using RP-HPLC and its mass was confirmed by MALDI mass spectrometry. The expected average mass of the linear peptide [M+H] 2316.3 m/z was observed. Tv1 was folded using thiol-assisted air oxidation reaction and purified by HPLC. The mass of folded Tv1, 2310.7 m/z, is reduced by 6 Da confirming that three intramolecular disulfide bonds had been formed. No differences were observed in synthesis and folding kinetics of the two Tv1 peptides with Ile or Leu at the third amino acid position, and both versions of Tv1 were used to determine the disulfide connectivity of the peptide.

Disulfide Mapping of Tv1

Due to the limited number of enzymatic cleavage sites and the presence of adjacent cysteine residues, traditional strategies for disulfide mapping such as tryptic digestion and acid hydrolysis were difficult to implement. The disulfide connectivity of Tv1 was independently determined by MS/MS mapping and NMR spectroscopy. For MS/MS mapping, a partial reduction and dual alkylation protocol was applied using reducing agent TCEP-HCl (Tris(2carboxyethyl)phosphine hydrochloride) and alkylating agents NEM (N-ethylmaleimide) and IAM (iodoacetamide). Chemically synthesized and oxidatively folded Tv1 peptide was first partially reduced at pH 3.0 with TCEP, and subsequently alkylated with NEM. The partially alkylated Tv1-NEM peptide was reduced further with TCEP at pH 7.0 and alkylated again with IAM this time. Dual NEM/IAM alkylation resulted in Tv1 peptide species that were labeled with 2, 4 or 6 NEM and IAM groups. The location of NEM and IAM modifications in each of the six partially reduced species was determined by matching the MS/MS b- and y-series ions to theoretical patterns. All six partially reduced species provided complementary, non-contradictory information and the resulting connectivity was determined to be Cys4-Cys20, Cys5-Cys21 and Cys7-Cys16. Tv1 has a cysteine scaffold similar to M Superfamily conotoxins but displays a disulfide pattern previously unknown in native cone snail peptides with a disulfide bridge formed between the two middle cysteines (Cys7 and Cys16) and a parallel 2-disulfide bond "staple" (Cys4-Cys20 and Cys5-Cys21) linking the N- and C-termini of the peptide.

Characterization of Tv1 by NMR Solution Structure Derivation

To confirm the disulfide bond connectivity derived from MS, the solution structure of Tv1 was derived using standard homonuclear proton NMR techniques on unlabeled folded synthetic peptide. Initial NMR experiments were carried out on Tv1 peptide containing either Ile or Leu at the third position. The spectra were very similar for both versions of the peptide, with the only differences found in the signals of the Ile3 and Leu3 residues themselves, indicating that both peptides adopt the same structure. Subsequent NMR structural calculations were carried out using only the Ile3 form of the peptide.

Proton assignments were obtained from 2D NOESY and TOCSY spectra, and carbon chemical shifts were assigned with the help of a natural-abundance $^{13}$C-HSQC spectrum. Initial structure calculation runs were carried out using only manually assigned Nuclear Overhauser Effect (NOE) distance restraints. Disulfide connectivities were then determined based on proximity of cysteine residues in the 10 lowest-energy structures and were in agreement with the disulfide bond pattern derived by MS analysis.

Direct evidence for the Cys7-Cys16 disulfide bond was also observed from NOE crosspeaks between the $H^N$ of Cys16 and the Ha of Cys7, as well as a number of connectivities to the two flanking residues, Gly6 and Tyr8. Once the disulfide linkages were determined, additional distance restraints for the disulfide bonds were introduced. The final round of structure calculations was run with covalent bonds between the connected cysteine side chains. A bundle of the 10 lowest-energy structures was obtained with an RMSD of 0.42 Å for backbone and 0.74 Å for all heavy atoms. A query for other peptide structures similar to the determined Tv1 structure using the software packages VAST or PDBeFOLD did not yield any hits, indicating that the structure of Tv1 represents a new fold for small peptide toxins. The most prominent and best-defined structural feature is a β-hairpin from Cys7 to Cys16 that is clamped together by the disulfide bond formed between these two residues. The remainder of the peptide wraps around the side chain aromatic ring of Tyr8, in particular through the formation of hydrophobic interactions with the side chains of Ile3 and Val15. The N- and C-terminal loops are clamped together in an antiparallel way through the Cys4-Cys20, Cys5-Cys21 double-disulfide bond arrangement, giving the whole teretoxin the shape of a flattened ellipsoid. Coordinates for the Tv1 structures have been submitted to the PDB and are available under accession code 2 mix.

Figure 1A:
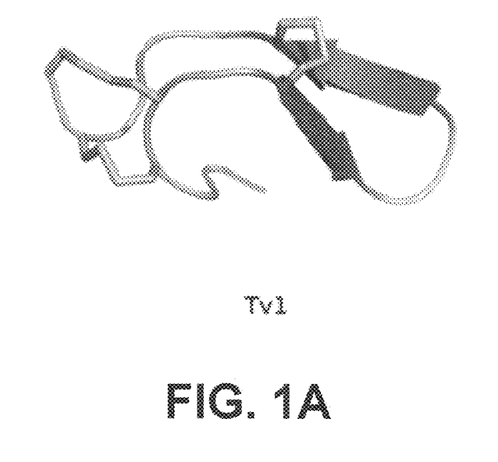
FIG. 1A, FIG. 1B, FIG. 1C and FIG. 1D provide a comparison of the structure of Tv1 with that of other M superfamily conotoxins.
Figure 1B:
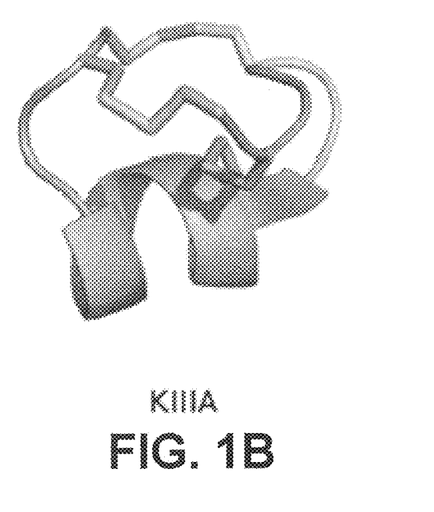
Figure 1C:
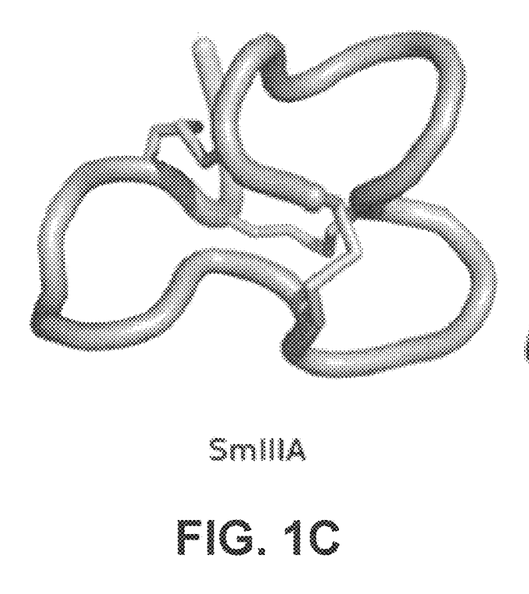
Figure 1D:
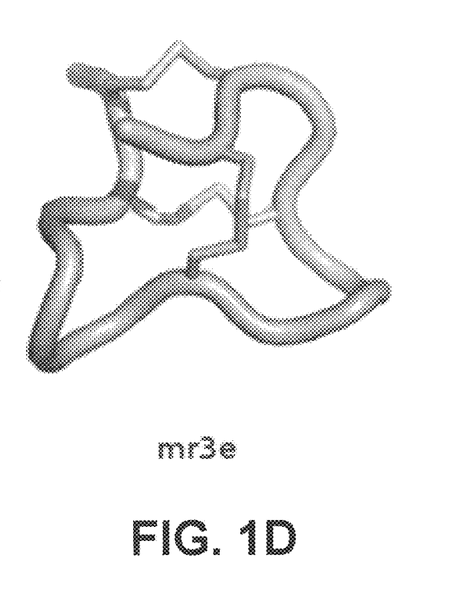

Although Tv1 has a cysteine scaffold similar to M Superfamily conotoxins, the observed differences in fold and disulfide bonding pattern are not surprising given the lack of sequence homology to M superfamily conotoxins. It is interesting to note that the loop between C3 and C4 is at least 4 amino acid residues longer in Tv1 compared to any of the other listed conotoxins, which is in agreement with the fact that these are the residues involved in the formation of the b-hairpin that is lacking in conotoxins. No β-strand structures are found in any of the other M-superfamily conotoxins (FIG. 1A; FIG. 1B; FIG. 1C and FIG. 1D). These figures provide a comparison of the NMR structure of Tv1 with that of M superfamily conotoxins SmIIIA, mr3e, and KIIIA and reveals significant structural differences between Tv1 and these conotoxins despite all having the same cysteine scaffold CC—C—C—CC. All structures are shown in cartoon representation. The only other example of Tv1's disulfide bond pattern was found in an active non-native minor refolding product for μ-conotoxin PIIIA. The 3D structures of both the native and non-natively refolded forms of PIIIA are very different from the structure of Tv1 as they contain segments of α-helix and no β-sheet structure. The difference between Tv1 and the PIIIA refolded product with the same disulfide bridge arrangement further supports the conclusion that Tv1 is representative of a new and unique group of peptide toxins.

Bioactivity Assay

To determine if synthetic Tv1 is biologically active, the peptide was injected into polychaete worms, which are the natural prey of terebrid snails. Injections of 20 μM Tv1 (Ile) into *N. virens* polychaete worms caused partial paralysis (Table 2). This finding is consistent with the recent study where crude terebrid venom extract exhibited nAChR inhibitory activity. Inhibition of nicotinic receptors at the neuromuscular junction can result in paralysis.

TABLE 2

Tv1 bioactivity in polychaete worms.

| Activity | % Time spent Tv1 (20 μM) | % Time spent NSS |
|---|---|---|
| at 0 | 0.995 | 1.45 |
| Between 0 and 1 | 74.47 | 0 |
| Between 1 and 2 | 19.98 | 0 |
| Between 2 and 3 | 4.55 | 98.55 |

Oxidative Folding of Tv1

A one-step thiol-assisted oxidation was used to prepare folded Tv1 peptide. The linear peptide (20 μM) was incubated in 0.1 M Tris-HCl, 0.1 M NaCl, 100 μM EDTA, 1 mM GSH, 1 mM GSSG, pH 7.5. The folding reaction was terminated by acidification with 8% formic acid at 15 min, 30 min, 1, 2, 3, 4, and 24 h and the folding yield monitored using UHPLC. A preparative scale folding reaction was then conducted at an optimized time of 2 h, and the folded peptide was purified using X-Bridge semipreparative column (as mentioned earlier). Elution was carried out at 5 mL/min with 15% buffer B and 85% buffer A for the first 5 min, then increasing buffer B to 35% in 45 min. The purity was confirmed using Acquity UHPLC column, and the molecular mass of the oxidized peptide was confirmed by MALDI-TOF.

Disulfide Mapping by Tandem MS/MS

A partial reduction and dual alkylation strategy was employed using reducing agent TCEP (Tris carboxy ethylphosphine hydrochloride, Thermo-Fisher) and alkylating agents NEM (N-ethylmaleimide, Sigma) and IAM (iodoacetamide, Sigma). Conditions for the partial reduction and alkylation of folded peptides were optimized modifying previous protocols. Briefly, 9 μl of folded peptide (1 μM) was dissolved in 0.1 M citrate buffer, pH 3.0 and 1 μl of TCEP (20 mM in 0.1 M citrate buffer, pH 3.0) was added to it. Reduction was carried out at 4° C. for 90 min and was terminated by injecting onto an RP-HPLC column [X-Bridge analytical column (5×150 mm, 5 mm particle size, Waters Corporation, Milford, Mass., USA)] and eluted with 20% buffer B in buffer A for 5 min, then increasing buffer B to 35% in 75 min. Six partially reduced peaks were each collected directly into microcentrifuge tubes containing 100 μl NEM (200 mM in 0.1 M citrate buffer pH 3) and incubated at 37° C. for 2 h in the dark. Partially reduced and alkylated reactions were then lyophilized and desalted to remove unreacted NEM using UHPLC. The desalted fractions were incubated with 100 mM TCEP at 55° C. for 1 h to completely reduce the NEM labeled peptide and alkylated with 275 μM IAM for 2 h at 37° C. in dark. The alkylation steps resulted in peptide species that were labeled with 2, 4 or 6 NEM or IAM groups. The labeled lyophilized species were suspended in 0.5% formic acid and subjected to LC-MS/MS analysis on 43 mm HPLC-Chip/Q-TOF using a 7 min gradient to resolve fully labeled species from those with incomplete alkylations. Data was collected in targeted and auto MS/MS mode and processed using molecular feature extraction (MFE) software to detect unique peptide features (MS and MS/MS spectra) followed by sequence matching on MassHunter Bioconfirm Qual B.05 software.

NMR Solution Structure Derivation

Samples for Nuclear Magnetic Resonance (NMR) studies were prepared by dissolving lyophilized oxidized peptide into either a 9:1 ratio of $H_2O:D_2O$ or in 100% $D_2O$ at a concentration of about 260 μM. Sample pH was adjusted to pH 6.0 and 50 μM trimethylsilyl propanoic acid was added as a reference compound. Spectral acquisition was carried out at 5° C. on a Varian Inova 600 MHz NMR spectrometer equipped with a cryogenically cooled HCN probe. 2D-TOCSY spectra were acquired in 90% $H_2O$ (64 scans with 1024×512 points) and $D_2O$ (48 scans with 1024×512 points) with spin-lock times of 60 ms, whereas 2D-NOESY spectra were acquired with mixing times of 200 ms in $H_2O$ with a matrix size of 1024×512 points in 64 scans and in $D_2O$ with a similar matrix size in 112 scans. A natural abundance $^1H^{13}C$ HSQC correlation spectrum was also acquired in 1024 scans with a matrix size of 1024×80 points. Acquired spectra were processed with NMRPipe and analyzed with CCPNmr Analysis. Proton assignments were made by comparison of TOCSY and NOESY spectra, and used to assign the $^{13}C$ chemical shifts through the HSQC spectrum. Distance restraints for structural calculations were obtained from 2 NOESY spectra: one spectrum collected in 90% $H_2O$ with a mixing time of 200 ms and another spectrum collected in $D_2O$ with a mixing time of 400 ms. Manual assignment was performed for about 90% of all NOE cross-peaks. Dihedral angle restraints were derived from the assigned chemical shifts using the software TALOS+. Structural calculations were carried out with ARIA2/CNS. Initial structural calculations were conducted using only the manual NOE assignments (with distances automatically calibrated by the software based on peak volumes) and without any restraints for the disulfide bonds. An ARIA2 run consisting of 8 iterations of simulated annealing followed by explicit water refinement of the 10 lowest-energy structures was performed. Disulfide connectivities were determined based on this initial structural bundle and included in the final round of structural calculations as covalent bonds. Eight iterations were performed in ARIA with 20 structures generated per iteration and the 7 lowest energy structures of each iteration forming the structural ensemble for the next iteration. For this run, NOE assignments were allowed to be automatically adjusted by the software during the calculation. For the last iteration, 100 structures were generated, and ten lowest-energy solutions were subjected to explicit solvent refinement. The quality of the final structural bundle was assessed by Procheck NMR.

Bioactivity Assay on Polychaete Worms

*Nereis virens* (polychaete worms) (less than 3.5 g) were maintained at 4° C. in salt water prior to injection. Worms were laid on a Styrofoam block and injected with an insulin syringe. A modified needle cap was used to maintain a consistent 1.5 mm depth of needle puncture. Worms were injected between the 5th and 7th segments on the ventral anterior end with the aim of targeting the ventral nerve cord. Control worms were injected with 12 μl of 0.9% normal saline solution (NSS). Lyopholized samples of Tv1 toxin were resuspended in NSS and diluted to a concentration of 20 μM which was confirmed using a ThermoScientific Nanodrop 2000c spectrophotometer. At least three worms were used for each trial—one saline control and two injected with Tv1 toxin for a total of three trials. After injection, the worms were transferred to side-by-side containers filled with room temperature salt water. The worm movements were then recorded by video in order to evaluate the effects of the toxin over a period of at least 3.5 hours. Varying temperature elicits different phenotypic responses from *N. virens*: water at 4° C. has an anesthetizing effect, while room temperature prompts a vigorous response. Taking the worms from 4° C. water and immersing them in room temperature water (25° C.) immediately after injection stimulates an active response from the worms, making it easier to recognize paralytic (or partially paralytic) effects induced by a novel toxin in the first minutes after injection. Worms were observed every other day for two weeks after injection. The recorded videos were analyzed blind by two independent observers; the activity of each worm over a small time interval was noted on a scale of 1-3, with 3 being extremely active and 1 being inactive. Each video was analyzed and annotated three times by each observer. Observations for each worm began at the time of injection. The numerical results of the two independent viewings were averaged together if results were similar, if two viewers disagreed, a third observer was employed to review the disputed section of video. Results of relative activity vs. time were plotted to quantify the phenotypic effects of the toxin and saline injection on *N. virens*. The data was also used to calculate what percentage of time each worm spent inactive (a rating of 1), active (an averaged rating of 1.5-2), and extremely active (rating 2.5-3) (Table 2).

In addition to Tv1's use as a cancer treatment, the peptide may also be useful as (1) An antagonist for ion channels and receptors such as sodium, potassium, and calcium channels, thermal channels, TRP channels, nicotinic acetycholine receptors, GABBA receptors and G-coupled receptors; (2) An agonist for ion channels and receptors such as sodium, potassium, calcium, TRP, nicotinic acetycholine receptors, GABBA receptors, G-coupled receptors; (3) an analgesic for pain; (4) an epileptic therapy; (5) a cardiovascular therapeutic agent; (6) an inhibitor of neurite outgrowth; (7) obesity and/or (8) diabetes.

There are over 400 different species of terebrids, each predicted to express between 50-200 different peptide toxins in their venom. With an integrated approach of mass spectrometry, chemical peptide synthesis, and NMR as applied to Tv1, it is now possible to access the substantial quantity of disulfide-rich peptides (greater than 80,000) in the Terebridae. The novel structural features of Tv1 suggest that teretoxins will reveal different mechanisms of action and different target specificities compared to disulfide-rich peptide toxins previously characterized and used as tools in neuroscience and as drug leads. In addition, an abundance of gastropods, including most species of the venomous marine conoidean snails, are smaller than 8 mm in shell size, highlighting the need for an efficient microscale mass spectrometry sequencing strategy. The sample limited integrated approach presented here can significantly enhance discovery and characterization of the vast disulfide-rich natural product peptide libraries produced by various venomous organisms.

Methods

Venom Extraction and De-Novo Sequencing

Four *Terebra variegata* snails were collected from the Las Perlas Archipelago in Panama and glands were dissected. Pooled crude venom contents from all 4 specimens were extracted with aid of light sonication in 30% acetonitrile/water acidified with 0.1% trifluoroacetic acid and centrifuged. The supernatant was lyophilized and stored at 20° C. An aliquot of crude venom was pressure loaded onto a self-packed PicoFrit column (New Objective) with integrated emitter tip (360 mm o.d., 75 mm i.d., 15 mm tip), packed with 6 cm of reverse-phase C18 material (Alltima C18 5 mm beads, Alltech Associates), rinsed for 10 min with 0.1 M acetic acid and subsequently gradient eluted with a linear gradient from 0 to 100% B in 30 min (A=0.1 M acetic acid, B=70% acetonitrile in 0.1 M acetic acid, flow rate 120 nL/min) into an LTQ Orbitrap XL with ETD (ThermoFisher Scientific), using a home-built micro electrospray source with a liquid junction.

The instrument was operated in data dependent mode cycling through full scan (300-2,000 m/z, single scan) followed by 8 MS/MS scans on the 8 most abundant ions from the immediate preceding full scan. Next, aliquots of reduced and iodoacetamide alkylated crude venom were pressure loaded onto a self-packed PicoFrit column (New Objective) with integrated emitter tip as described above and eluted using the same gradient as above into the LTQ Orbitrap XL with ETD. Instrument was operated in a data dependent mode cycling through a full scan (300-2,000 m/z, single scan) followed by 8 MS/MS scans on the 4 most abundant ions from immediate preceding full scan. The instrument was programmed to acquire first 4 CAD and then 4 ETD spectra on the 4 most abundant ions. The cations were isolated with a 2-Da mass window and set on a dynamic exclusion list for 30 seconds after they were first selected for MS/MS. Target value for MS/MS was set to $10^4$ cations and $10^6$ anions of fluoranthene. For CAD an activation time of 30 ms was chosen. For ETD the ion/ion reaction time was set to 100 ms. In both cases 4 scans were averaged per MS/MS spectrum. In a majority of cases, complete sequence elucidation after this initial analysis was not possible, but based on this initial screen optimal charge states for subsequent targeted ETD analysis were chosen. For subsequent analysis either reduced, iodoacteamide alkylated, or dimethyl lysine analog versions of toxin were pressure loaded onto the self-packed columns as described above. The column was rinsed for 10 min (for reduced or iodoacetamide alkylated toxins) or for 20 min (for lysine dimethyl analog versions of toxins) with 0.1 M acetic acid and gradient eluted into the LTQ XL as described above. To obtain higher quality MS/MS spectra in this second analysis, 12 scans were averaged and the data acquired in high resolution with 7,500 resolution setting. The spectra were manually interpreted.

Synthesis and Purification of Tv1

Tv1 peptide was synthesized by microwave assisted Fmoc SPPS on a CEM Liberty synthesizer using standard side chain protection. Standard Fmoc cysteine with side chain protecting group Trityl (Fmoc-Cys (Trt)-OH) was used for all cysteine residues in the Tv1 peptide. Following treatment of peptidyl resin with Reagent K [92.5% TFA (Trifluoroacetic acid), 2.5% TIS (Triisopropylsilane), 2.5% EDT (1,2 Ethanedithiol) and 2.5% water, 4 hr)] and cold ether precipitation, crude Tv1 was purified by RP-HPLC using an X-Bridge semipreparative column (10×150 mm, 5 μm particle size, Waters Corporation, Milford, Mass., USA). Elution was carried out at 5 mL/min with 20% buffer B (80% Acetonitrile, 0.1% TFA) and 80% buffer A (0.1% TFA) for the first 5 min, then increasing buffer B to 35% in 45 min. HPLC buffer composition remained the same all through the work. Purity of collected peptide was confirmed by RP-UHPLC using an Acquity UPLC (BEH 300 C18 1.7 μm, Waters Corporation) column and eluted using a linear gradient from 0% to 75% buffer B in 3.5 min. The identity of synthesized peptide was confirmed by molecular mass measurement of purified peptide using MALDI-TOF (Waters, Micromass, CHαCN matrix).

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for treating liver cancer, the method comprising administering a peptide to a patient with liver cancer, the peptide comprising SEQ ID NO: 1 (TRX$_3$CCGCYWNGSKDVCSQSCC) wherein the peptide has one hundred or fewer residues and X$_3$ is I or L.

2. The method as recited in claim 1, wherein the peptide has fifty or fewer residues.

3. The method as recited in claim 1, wherein the patient is a human patient.

4. A method for treating liver cancer, the method comprising administering a peptide to a patient with liver cancer, the peptide consists of SEQ ID NO: 1 (TRX$_3$CCGCYWNGSKDVCSQSCC) wherein X$_3$ is I or L.

5. The method as recited in claim 4, wherein the patient is a human patient.

6. A method for treating liver cancer, the method comprising administering a peptide to a patient with liver cancer, the peptide comprising SEQ ID NO: 1 (TRX$_3$CCGCYWNGSKDVCSQSCC) wherein the peptide has thirty or fewer residues and X$_3$ is I or L.

7. The method as recited in claim j, wherein the patient is a human patient.

* * * * *

UNITED STATES PATENT AND TRADEMARK OFFICE
CERTIFICATE OF CORRECTION

PATENT NO. : 9,610,319 B2  
APPLICATION NO. : 14/870271  
DATED : April 4, 2017  
INVENTOR(S) : Mande Holford et al.

Page 1 of 1

It is certified that error appears in the above-identified patent and that said Letters Patent is hereby corrected as shown below:

In the Claims

Column 21, Claim 7, Line 6, change "The method as recited in claim j" to -- The method as recited in claim 6 --

Signed and Sealed this
Sixteenth Day of May, 2017

Michelle K. Lee
*Director of the United States Patent and Trademark Office*